(12) United States Patent
Farr et al.

(10) Patent No.: US 9,778,276 B2
(45) Date of Patent: Oct. 3, 2017

(54) LIQUID HANDLING DEVICE

(75) Inventors: Isaac Farr, Corvallis, OR (US); Erick B. Kinas, Vancouver, WA (US); Kevin F. Peters, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1284 days.

(21) Appl. No.: 12/742,893

(22) PCT Filed: Nov. 20, 2007

(86) PCT No.: PCT/US2007/024355
§ 371 (c)(1),
(2), (4) Date: May 13, 2010

(87) PCT Pub. No.: WO2009/067103
PCT Pub. Date: May 28, 2009

(65) Prior Publication Data
US 2010/0255600 A1    Oct. 7, 2010

(51) Int. Cl.
*G01N 35/10* (2006.01)

(52) U.S. Cl.
CPC ..... *G01N 35/1011* (2013.01); *G01N 35/1065* (2013.01); *Y10T 29/49826* (2015.01)

(58) Field of Classification Search
CPC ............. G01N 21/6452; G01N 35/028; G01N 21/253; G01N 35/1074; G01N 21/6428; G01N 21/6456; G01N 2201/0846; G01N 2201/1248; G01N 2201/6482; G01N 2201/7773; G01N 21/552; G01N 21/47; G01N 21/55; G01N 2021/212; G01N 2015/1479; G01N 2035/0424
See application file for complete search history.

(56) References Cited

U.S. PATENT DOCUMENTS

| | | | |
|---|---|---|---|
| 6,814,933 B2 * | 11/2004 | Vuong | 422/82.05 |
| 6,878,341 B2 | 4/2005 | Kowallis | |
| 6,890,485 B1 | 5/2005 | Stylli | |
| 7,025,933 B2 | 4/2006 | Ganz | |
| 2004/0208795 A1 | 10/2004 | Toi | |
| 2009/0027693 A1 * | 1/2009 | Dailey et al. | 356/620 |

FOREIGN PATENT DOCUMENTS

| | | |
|---|---|---|
| EP | 0210014 | 1/1987 |
| KR | 0091966 | 11/2004 |
| KR | 0091967 | 11/2004 |
| KR | 0007071 | 1/2005 |

OTHER PUBLICATIONS

Hezzini, "Measurement Sensors: Specular vs. Diffusive": Panasonic Tech Insights: Electronic Components, Factory Automation and Lighting Solutions, Dec. 2011 http://www.pidtechinsights.com/2011/12/07/measurement-sensors-specular-vs-diffuse/.*

Miura et al. in "Simultaneous Estimation of Reflectance Parameters from Images", no publication date; http://delivery.acm.org/10.1145/1180000/1179737/p100-miura.pdf?ip=151.207.250.11&acc=ACTIVE%20SERVICE&CFID=188980326&CFTOKEN=21244882&_acm_=1351627279_ef970bd0bc7e4c6660c4aa4fbd98223.*

* cited by examiner

*Primary Examiner* — Yelena G Gakh
(74) *Attorney, Agent, or Firm* — Law Office of Ingrid M. McTaggart

(57) ABSTRACT

A liquid handling device that determines a position of a tray utilizing light reflected from structural features of the tray.

9 Claims, 1 Drawing Sheet

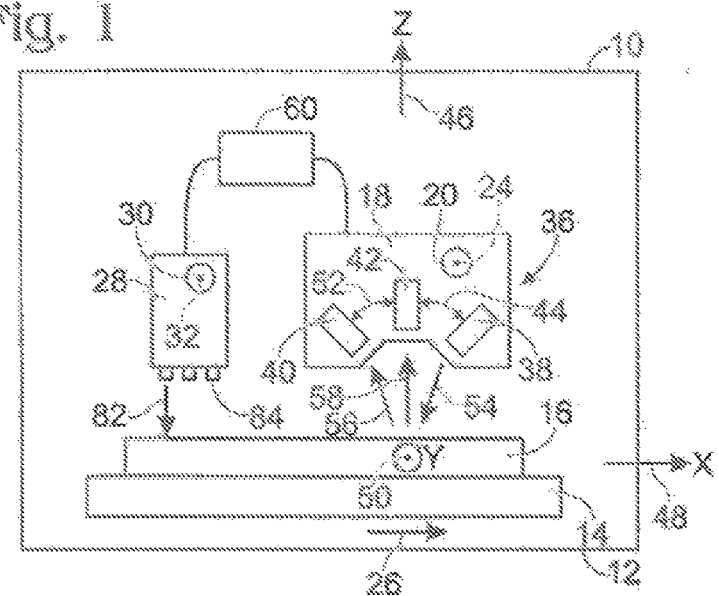
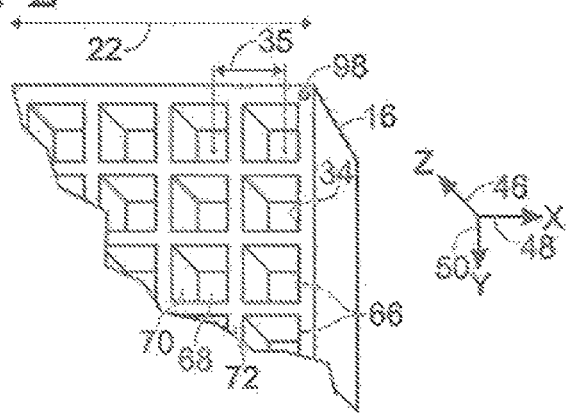
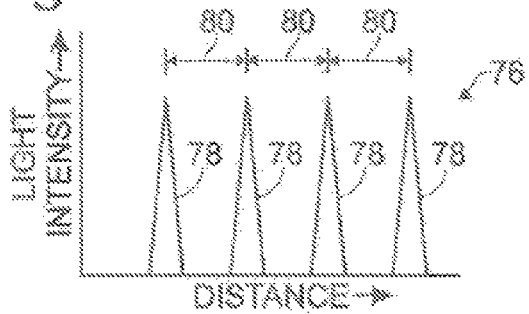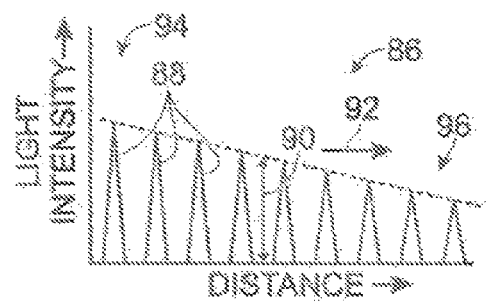

LIQUID HANDLING DEVICE

BACKGROUND

Liquid handling devices may automatically deposit liquid into multiple wells of a well tray, such as a well plate. Misalignment of the well tray within the liquid handling device may result in misdeposition of liquid into the well tray, such as no liquid deposited into some wells, too much liquid deposited into other wells, liquid deposited ineffectively onto the interior walls of wells, and some liquid deposited over the edge of the well tray. Moreover, these potential problems of well tray misalignment may be exacerbated when the dispensing location is desired to be near the perimeter boundary of the well. Dispensing near the well perimeter is sometimes desired, for example, when the dispenser is moving or when the dispenser comprises multiple dispensing nozzles that are located at different positions over a well. It may be desirable to reduce misdeposition of liquid into a well tray in a liquid handling device.

BRIEF DESCRIPTION OF THE DRAWINGS

FIG. 1 is schematic side view of one example embodiment of a liquid handling device.

FIG. 2 is a top perspective view of one example embodiment of a specimen tray of a liquid handling device.

FIG. 3 is one example embodiment of a reflected light signal reflected from a specimen tray.

FIG. 4 is another example embodiment of a reflected light signal reflected from a specimen tray.

DETAILED DESCRIPTION OF THE DRAWINGS

FIG. 1 is schematic side view of one example embodiment of a liquid handling device 10. Device 10 may be an automatic liquid handling (ALH) device including a housing 12 that includes therein a tray support 14 adapted for supporting thereon a specimen tray 16, such as a well tray. Device 10 may further include a carriage 18 mounted on a carriage rod 20 for movement across a width 22 (see FIG. 2) of tray 16 along a carriage rod axis 24. Tray support 14 may be adapted to move tray 16 in a direction 26, for example, though housing 12. Accordingly, movement of tray 16 in direction 26, and movement of carriage 18 along carriage rod axis 24 may allow carriage 18 to be positioned above any region of tray 16 as may be desired. Device 10 may further include a liquid deposition device 28, such as a printhead, that may be mounted on a second carriage rod 30 for movement along a second carriage rod axis 32. Accordingly, movement of tray 16 backwards and forwards in direction 26, and movement of deposition device 28 along second carriage rod axis 32 may allow deposition device 28 to be positioned above any region of tray 16 as may be desired.

In another embodiment, the specimen tray may be movable with respect to the liquid dispensing device so as to allow positioning of the dispensing device above any region of the specimen tray as may be desired.

Automated liquid handling device 10 may utilize specimen tray 16 to receive small amounts of liquid automatically injected into each well from deposition device 28. The specimen tray 16 may be utilized to perform capillary and nano liquid chromatography, genomic amplification, biological assays of experimental drug activity, or cell culture applications utilizing light microscopes, for example. The specimen tray 16 may include several hundred, or thousands, of individual wells 34 (some of which are shown in FIG. 2) that may have center-to-center well offsets 35 (see FIG. 2) of 4.5 mm, or even 2.25 mm. Accordingly, even slight misalignment of the specimen tray 16 on tray support 14, such as a rotation of less than 0.3 degrees about the z-axis 46, may result in poor liquid dispensing. In other instances, much smaller rotations, for example, as small as approximately 0.01 degrees, may result in poor liquid dispensing. This may happen under extreme instances, for example, when the center-to-center offsets of dispensing locations is as small as fifty microns and no accounting for misalignment is made. Poor liquid dispensing may include no liquid deposited into some wells, too much liquid deposited into other wells, dispensing onto walls of wells, and some liquid deposited over the edge of the well tray. In order to reduce misdeposition of liquid into specimen tray 16, Applicants' liquid handling device 10 includes a tray position detection system 36.

Still referring to FIG. 1, tray position detection system 36 may be housed within carriage 18 and may include a light source 38, such as a light emitting diode (LED), and one or more light sensors 40 and 42. In the embodiment shown, first light sensor 40 is a spectral light sensor and second light sensor 42 is a diffuse light sensor. In other embodiments, other light sources and/or sensors may be utilized, such as a monochromatic light sensor, a photo diode array, a CCD sensor, a CMOS sensor, an LED light source, a incandescent light source or a florescent light source, for example. Light source 38 may be positioned at an angle 44 of thirty degrees, for example, from a z-axis 46 perpendicular to x and y axes, 48 and 50 respectively, of specimen tray 16. Second light sensor 42 may be positioned along perpendicular axis 46 and first light sensor 40 may be positioned at an angle 52 of thirty degrees, for example, from perpendicular axis 46. In other embodiments, other angles may be utilized for the source(s) and/or sensor(s) position as may be desirable for a particular application. In use, a light beam 54 is projected from light source 38 toward specimen tray 16 and the reflected light is sensed by sensors 40 and 42.

FIG. 2 is a top perspective view of one portion of an example embodiment of a specimen tray 16 of the liquid handling device 10 of FIG. 1. Specimen tray 16 may include structural features of individual wells 66, such as a well floor 68, one or more well side walls 70 and ribs 72 positioned between each of adjacent individual wells 66. In the embodiment shown, ribs 72 may be defined as the horizontal, upper surface of side walls 70. As light beam 54 (FIG. 1) is projected to these structural features such as features 68, 70, and/or 72 of individual wells 66, the light beam 54 may be reflected differently from different ones of the structural features such as features 68, 70, and/or 72. The differences in the reflected light reflected from these structural features such as features 68, 70, and/or 72 of the individual wells 66 may be utilized to determine the position and/or orientation of specimen tray 16 within device 10.

Referring again to FIG. 1, in the example embodiment shown, spectral reflected light 56 that is reflected from structural features such as features 68, 70, and/or 72 of tray 16 is detected by sensor 40 and diffuse reflected light 58 that is reflected from structural features of tray 16 is detected by sensor 42. The reflected light 56 and 58 detected by sensors 40 and 42, respectively, is then analyzed by a controller 60 connected to sensors 40 and 42. Each of the reflected light signals received by controller 60 may include information such as a signal peak height and/or a signal peak location, that may correspond to or represent structural features such as features 68, 70, and/or 72.

FIG. 3 is one example embodiment of a reflected spectral light signal 76 of spectral reflected light 56 (FIG. 1) reflected from specimen tray 16. Controller 60 may analyze reflected spectral light signal 76 and determine that each of individual peaks 78 are spaced a distance apart 80 of approximately 4.5 mm, for example. This spacing distance 80 may match the actual spacing distance of individual ribs 72 (see FIG. 2) of specimen tray 16. This measured peak spacing distance 80, therefore, may be interpreted by controller 60 that the peaks 78 of reflected spectral light signal 76 represent light reflected from each ribs 72 (see FIG. 2). Accordingly, by determining a position of each of peaks 78, controller 60 may determine the position of each of ribs 72, and thereby determine the position of specimen tray 16 on tray support 14. Utilizing this positional information, controller 60 may direct liquid deposition device 28 to deposit liquid 82 (FIG. 1) out of individual orifices 84 of deposition device 28 and into individual ones of wells 66. Due to the known location of the specimen tray 16 and individuals wells 66 therein, misdeposition of liquid 82 is reduced. In particular, instances of no liquid deposited into some wells 66, too much liquid 82 deposited into other wells 66, dispensing onto the walls of wells, and some liquid 82 deposited over an edge of the specimen tray 16, may be reduced or even eliminated.

Referring again to FIG. 1, in one embodiment, carriage 18 may be moved across specimen tray 16, during which time one or both of light sensors 40 and 42 may sense a reflected light that is reflected from specimen tray 16. In one example, light sensor 40 may sense a reflected spectral light at locations spaced by a distance of at most $\frac{1}{500}$th an inch, more particularly, may sense a reflected spectral light at locations spaced by a distance of approximately $\frac{1}{600}^{th}$ of an inch along specimen tray 16. This may be accomplished by use of a linear encoder strip (not shown) positioned adjacent carriage 18. Carriage 18 may be moved along carriage rod 20 at a speed of approximately ten inches per second. Accordingly, in one embodiment, the signal 76 represented by FIG. 3 may show an intensity of reflected spectral light measured at every $\frac{1}{600}^{th}$ of an inch across specimen tray 16, wherein some of the measurements may record no measurable reflected light and may be represented as a "zero" intensity reading shown between each of visible peaks 78.

FIG. 4 is one example embodiment of a reflected diffuse light signal 86, for example, of diffuse reflected light 58 reflected from specimen tray 16. Controller 60 may analyze reflected diffuse light signal 86 to determine that each of individual peaks 88 define a peak height 90, wherein the peak height 90 of each successive peak 88, as measured in a direction 92, steadily decreases. In other words, the peak intensity of each peak, as measured in direction 92, decreases. This pattern of decreased peak intensity may be interpreted by controller 60 that well tray 16 is spaced a close distance to light source 38 (see FIG. 1) in a first edge region 94 (represented by the left region of FIG. 4) and that well tray 16 is spaced a further distance from light source 38 (see FIG. 1) in a second edge region 96 (represented by the right region of FIG. 4). Accordingly, controller 60 may determine that well tray 16 is rotated about the y axis 50 such that tray 16 is not positioned flat on tray support 14. Utilizing this positional information, controller 60 may sound an alarm or provide an error message to an operator, or may direct liquid deposition device 28 to deposit liquid 82 out of individual orifices 84 of deposition device 28 and into individual ones of wells 66 that are positioned within an appropriate liquid receiving range from liquid deposition device 28.

Another interpretation of this pattern of decreasing peak height 90 or intensity, as measured in a direction 92, may be interpreted by controller 60 that well tray 16 is rotated about a z-axis such that the light sensor is sensing less light reflected from a rib 72 because each successive rib may be positioned further from the light beam 54 of light source 38, as the sensor is moved in direction 92. The interpretation of the light sensed by the light sensors may be determined by multiple baseline readings stored within controller 60 for a variety of misalignment situations.

In different embodiments of liquid handling device 10, spectral and/or diffuse reflected light may be analyzed by controller 60. In one embodiment wherein specimen tray 16 may be manufactured of a black material, reflected spectral light 56 may provide easily readable peaks 78 (FIG. 3) for analysis by controller 60. In another embodiment wherein specimen tray 16 may be manufactured or a clear material, reflected diffuse light 58 may provide easily, readable peaks 88 (FIG. 4) for analysis by controller 60. Moreover, other variables, such as the distance of the light source and/or sensors from the specimen tray, the type, direction and/or intensity of the light projected to the specimen tray, and the type of specimen tray, may also determine the analysis conducted by controller 60.

Determination of the positions of individuals wells 66 of specimen tray 16 may allow a correction for specimen tray misalignment, may allow confirmation of specimen tray format (the size, shape, and number of wells), may allow calibration of a feed roller mechanism for driving specimen tray 16 through housing 12 (comparison of the specimen tray position before and after movement), may allow for dispensing nearer the well perimeter and from a greater number of nozzle positions, and may allow for use of a lower cost feed roller mechanism due to the ability to locate the specimen tray after positioning.

Given this capability to determine the positions of reflective features of a specimen tray, in another embodiment, it may also be beneficial to provide specimen trays with reflective features 98, in addition to wells, that are amenable to this reflective reading scheme. The reflective features 98 may include a reflective material utilized to manufacture the tray, and/or a reflective marking printed with a reflective ink, such as a printed datum point 98, for example. These reflective features of a specimen tray may be used to align the tray and/or to identify it.

Other variations and modifications of the concepts described herein may be utilized and fall within the scope of the claims below.

We claim:
1. A liquid handling device, comprising:
a tray support;
a specimen tray positioned on said tray support, said specimen tray including a plurality of individual wells;
a light source that directs a light toward said specimen tray;
a first light sensor that receives light that is reflected from structural features of said plurality of individual wells of said specimen tray;
a second light sensor adjacent to said specimen tray that receives reflected light from structural features of said plurality of individual wells of said specimen tray; and
a controller that utilizes said reflected light from said first and second light sensors to determine a position of said specimen tray and each of said plurality of individual wells on said tray support.

2. The device of claim 1 wherein said specimen tray comprises a well tray and each of said plurality of individual wells includes a side wall and a floor.

3. The device of claim 1 wherein said reflected light from said first and second light sensors defines a light signal of peaks, wherein said peaks correspond to said plurality of individual wells of said specimen tray, and wherein said peaks are utilized by the controller in the determination of the position of said specimen tray and each of said plurality of individual wells.

4. The device of claim 1 further comprising a liquid deposition device including a plurality of deposition orifices, wherein individual ones of said deposition orifices are controlled by said controller to deposit liquid into said plurality of individual wells of said specimen tray, based on said position of said specimen tray as determined by said controller.

5. The device of claim 1 further comprising a positioning device controlled by said controller to move said specimen tray into a controlled position relative to said first and second light sources.

6. The device of claim 1, said controller to sound an alarm in response to in response to said specimen tray being misaligned on said tray support.

7. The device of claim 1, wherein said structural features include a well floor, a well side wall, and a rib positioned between individual wells of the specimen tray.

8. The device of claim 1, further comprising a carriage to house said first and second light sensors, wherein said carriage is moveably positioned on a first carriage rod for movement across said specimen tray.

9. The device of claim 8, further comprising a liquid deposition device controlled by said controller, adjacent to said specimen tray, and moveably located on a second carriage rod for movement across said specimen tray, the liquid depositing device to deposit liquid into at least one of said plurality of individual wells based on said positions of said specimen tray and each of said plurality of individual wells.

\* \* \* \* \*